(12) United States Patent
Lesage

(10) Patent No.: US 9,132,066 B2
(45) Date of Patent: Sep. 15, 2015

(54) INSERTION MATERIAL INTENDED FOR WIDENING THE GINGIVAL CREVICE

(76) Inventor: Patrick Lesage, Saint Malo (FR)

(*) Notice: Subject to any disclaimer, the term of this patent is extended or adjusted under 35 U.S.C. 154(b) by 0 days.

(21) Appl. No.: 13/574,170

(22) PCT Filed: Jan. 20, 2011

(86) PCT No.: PCT/FR2011/050106
§ 371 (c)(1),
(2), (4) Date: Jul. 19, 2012

(87) PCT Pub. No.: WO2011/089362
PCT Pub. Date: Jul. 28, 2011

(65) Prior Publication Data
US 2012/0295222 A1 Nov. 22, 2012

(30) Foreign Application Priority Data

Jan. 21, 2010 (FR) ...................................... 10 50395

(51) Int. Cl.
| | |
|---|---|
| *A61K 33/06* | (2006.01) |
| *A61K 6/00* | (2006.01) |
| *A61K 6/097* | (2006.01) |
| *A61K 33/14* | (2006.01) |
| *A61L 26/00* | (2006.01) |

(52) U.S. Cl.
CPC .............. *A61K 6/0011* (2013.01); *A61K 6/0058* (2013.01); *A61K 6/0067* (2013.01); *A61K 6/097* (2013.01); *A61K 33/06* (2013.01); *A61K 33/14* (2013.01); *A61L 26/0023* (2013.01)

(58) Field of Classification Search
CPC ... A61K 2300/00; A61K 8/19; A61K 6/0011; A61K 6/097; A61K 33/06; A61K 33/14; A61K 6/00; A61K 6/0058; A61Q 11/00; A61L 26/0023
USPC .............................. 424/445, 685; 433/136, 80
See application file for complete search history.

(56) References Cited

U.S. PATENT DOCUMENTS

| | | | |
|---|---|---|---|
| 5,362,495 A | 11/1994 | Lesage | |
| 6,187,294 B1 * | 2/2001 | Penner | 424/49 |
| 7,029,690 B1 * | 4/2006 | Wehrli | 424/435 |
| 2004/0253313 A1 * | 12/2004 | Ueda et al. | 424/484 |
| 2005/0084551 A1 * | 4/2005 | Jensen et al. | 424/769 |
| 2005/0287494 A1 | 12/2005 | Yang et al. | |
| 2007/0264315 A1 * | 11/2007 | Fournie et al. | 424/445 |
| 2008/0299199 A1 * | 12/2008 | Bar-Shalom et al. | 424/484 |
| 2011/0046262 A1 * | 2/2011 | Bublewitz et al. | 523/121 |

FOREIGN PATENT DOCUMENTS

| | | |
|---|---|---|
| DE | 3736155 | 5/1989 |
| EP | 0477244 | 4/1992 |
| EP | 2036533 | 3/2009 |
| WO | WO 90/15587 | 12/1990 |
| WO | WO 2007/128926 | 11/2007 |
| WO | WO 2008/021740 | 2/2008 |
| WO | WO 2009092568 A2 * | 7/2009 |

* cited by examiner

*Primary Examiner* — Frederick Krass
*Assistant Examiner* — Tracy Liu
(74) *Attorney, Agent, or Firm* — Hamre, Schumann, Mueller & Larson, P.C.

(57) ABSTRACT

The present invention relates to a novel insertion material intended for widening the gingival crevice. According to the invention, this material consists of a hydrophilic paste comprising, expressed as percentage by weight relative to the total weight of the material:
  between 5 and 15% of an astringent;
  between 25 and 50% of a specifically chosen texturizing agent;
  between 30 and 60% of water; and
  between 0 and 20% of a humectant;
the total amount of water and humectant being between 35 and 65% by weight relative to the total weight of the material; said insertion material having the following release profile for the astringent:
  less than 20% of astringent released after 5 min;
  less than 40% of astringent released after 10 min;
  less than 50% of astringent released after 15 min;
  less than 60% of astringent released after 30 min;
  less than 80% of astringent released after 60 min.

25 Claims, 1 Drawing Sheet

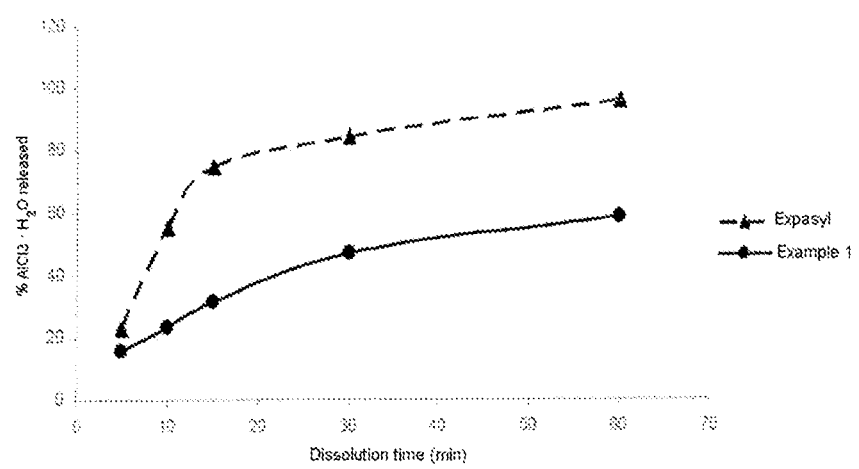

INSERTION MATERIAL INTENDED FOR WIDENING THE GINGIVAL CREVICE

The subject of the present invention is a novel insertion material that is used for widening the gingival crevice, substantially without bleeding. It can be used in the dental field.

The gingival crevice is a virtual space, located between the tooth and the gum, that it is necessary to widen in order to carry out various dental care procedures, for example prior to taking an impression.

Generally, widening of the gingival crevice can be obtained:
either by eviction, for example using an electric bistoury or a diamond charged drill;
or by retraction, by inserting into the gingival crevice a preformed material, such as cotton cord optionally impregnated with a solution intended to promote retraction, or an injectable composition capable of hardening by chemical reaction or by physical swelling.

The patent EP 0 477 244 describes an insertion material of original design which is in the form of a biocompatible and injectable paste comprising essentially:
an agent intended to absorb fluids, such as in particular kaolin clay (or China clay) or an algal flour;
water;
an astringent, preferably aluminum chloride, intended to facilitate the stopping of bleeding through its retraction action, resulting in good surface hemostasis.

This patent led to the development, and then the marketing of the product known as Expansyl® which opened up a new route of treatment in all indications of temporary sulcular opening.

This product is in fact particularly advantageous, in particular in comparison with the materials that can be hardened by chemical reaction, owing to its simplicity of use (absence of premixing) and its rapid action (no hardening time).

In addition, since it contains aluminum chloride, the Expasyl® product results in opening of the sulcus with excellent hemostasis.

However, the Expasyl® product has a certain number of drawbacks.

First of all, owing to the very hydrophilic and water-soluble nature of kaolin clay, this product must be kept away from saliva in order to avoid premature dilution thereof, thus creating a situation of discomfort for the patient, who must avoid closing the mouth during its use.

For the same reasons, once put in place, this product cannot be used together with an instrument comprising a water spray.

Whatever the precautions taken, it has been noted that the Expasyl® product is diluted with saliva and sulcular fluids, losing its consistency and its effectiveness after approximately two minutes, limiting accordingly the working time for the dentist.

Moreover, removal of this product after use takes a relatively long time and requires a large amount of water, in particular in order to avoid any deposit of kaolin on the dentine, which can interfere for example with bonding, and also in order to remove the chloride which can interfere with the setting of impression materials of the polyether category.

The use of a large amount of water leads to disintegration of the product and the release of its constituent components, and in particular of the aluminum chloride. As it happens, aluminum chloride has a particularly unpleasant and persistent taste and can lead to irritation of the mucous membranes.

A material that can be used to form a dressing on the oral mucous membranes or on the skin, consisting of a biocompatible paste containing, as essential constituent, natural kaolin, a humectant and a hydrogel-forming agent, preferably colloidal silica, is also known through document WO 2007/128926. This material contains between 35 and 55% by mass of kaolin and disintegrates very rapidly in the presence of water. As a result, it has the same drawbacks as the Expasyl® product. Furthermore, this material does not allow opening of the sulcus. It cannot therefore be used in the applications envisioned by the present invention.

In this context, the objective of the present invention is to solve the technical problem consisting of the provision of a novel insertion material having the advantages of the Expasyl® product without suffering from the same drawbacks.

It has been discovered, and this constitutes the basis of the present invention, that it is possible to solve this technical problem in a manner that is entirely satisfactory and capable of being readily implemented on an industrial scale by incorporating the astringent into a matrix allowing slow release of the astringent and having sufficient cohesion in an aqueous medium to avoid the loss of its mechanical properties for a period of time compatible with any type of treatment.

Thus, according to a first aspect, the subject of the present invention is an insertion material intended for widening the gingival crevice, characterized in that it consists of a hydrophilic paste comprising, expressed as percentage by weight relative to the total weight of the material:
between 5 and 15%, preferably between 6 and 12% of an astringent, preferably aluminum chloride;
between 25 and 50%, preferably between 30 and 45% of a texturizing agent chosen from:
hydrophilic biopolymers;
hydrophilic biopolymers combined with plant fibers;
hydrophilic biopolymers combined with plant fibers and with polyvinyl alcohol;
plant fibers combined with polyvinyl alcohol;
between 30 and 60%, preferably between 30 and 55% of water; and
between 0 and 20%, preferably between 5 and 18% of a humectant;
the total amount of water and humectant being between and 65%, preferably between 40 and 60% by weight relative to the total weight of the material;
said insertion material having the following release profile for the astringent, measured according to the dissolution method described in the European Pharmacopoeia, 6th edition (Ph. Eur. 2.9.3 (01/2008)) at 150 rpm in 700 ml of purified water at 37° C.:
less than 20% of astringent released after 5 min;
less than 40% of astringent released after 10 min;
less than 50% of astringent released after 15 min;
less than 60% of astringent released after 30 min;
less than 80% of astringent released after 60 min.

As is understood, the originality of the material in accordance with the present invention lies firstly in the nature of the matrix-forming texturizing agent of which it is composed.

This texturizing agent can consist:
either of one or more hydrophilic biopolymers;
or of one or more hydrophilic biopolymers combined with plant fibers;
or of one or more hydrophilic biopolymers combined with plant fibers and with polyvinyl alcohol;
or of plant fibers combined with polyvinyl alcohol.

In the insertion material in accordance with the invention, the texturizing agent represents between 25 and 50%, preferably between 30 and 45% by weight, relative to the total weight of the material.

The hydrophilic biopolymers that can be used in the context of the present invention are advantageously chosen from polysaccharides of natural origin, preferably of food grade, having a gelling or thickening power, and in particular from the group consisting of pectins; galactomannans of guar, locust bean or tara seeds; scleroglucan; xanthan; carrageenans, and mixtures thereof.

This biopolymer is advantageously chosen in order to obtain a matrix having rheological properties that are stable over time. To this effect, the texturizing agent in accordance with the invention is free of or contains only a small amount, less than 10% by weight relative to the weight of the texturizing agent, of alginates.

This is because it has been observed that gels that can be formed from alginates are irreversible and do not exhibit a consistency stable over time that is compatible with their use in the context of the invention.

Preferably, the hydrophilic biopolymer will be chosen from carrageenans.

The carrageenans are generally obtained by hot extraction of red algae of the family Rhodophyceae, in particular of *Chondrus* and *Eucheuma*.

They are copolymers of D-galactose ether sulfate and of 3,6-anhydro-D-galactose which can be in the form of salts, in particular potassium or calcium salts.

Advantageously, the carrageenans used in the context of the invention are of iota type, such as, in particular, the products sold by the company FMC Biopolymere under the names Viscarin® or Gelcarin®.

Excellent results have been obtained in the context of the present invention with the product Viscarin® PC 389.

When the texturizing agent consists exclusively of one or more hydrophilic biopolymers, it advantageously represents 40 to 50% by weight, and more preferably approximately 45% by weight, relative to the total weight of the insertion material.

The plant fibers that can be used in the context of the present invention are advantageously chosen from pea fibers and oat fibers.

Such products are well known in the cosmetics field and are, for example, sold by the company Beacon CMP under the name Tech-O®.

In the context of the present invention, the plant fibers are used either in combination with one or more hydrophilic polymers, or in combination with polyvinyl alcohol, or else in combination with one or more hydrophilic biopolymers and polyvinyl alcohol.

Generally, the weight ratio of the plant fibers to the hydrophilic biopolymers is between 1:1 and 1.5:1, preferably about 1.25, while the weight ratio of the plant fibers to the polyvinyl alcohol is generally between 12:1 and 20:1, preferably about 15:1.

The polyvinyl alcohol that can be used in the context of the present invention is preferably of cosmetic or pharmaceutical grade.

Advantageously, this product should have a relatively high viscosity, for example of about at least 20 mPa·s in an aqueous solution at 4%.

Among the polyvinyl alcohols that can be used in the context of the present invention, mention may be made of the products sold under the name Gohsenol® EG, such as, in particular, the products Gohsenol® EG-25, Gohsenol® EG-30 and Gohsenol® EG-40.

The polyvinyl alcohol is generally used:
  in an amount of between 1 and 3% by weight, preferably 1.5 to 3% by weight, and more preferably of approximately 2% by weight, relative to the total weight of the material when it is combined with plant fibers; and
  in an amount of between 0.5 and 2% by weight, preferably of about 1% by weight when it is used in combination with plant fibers and one or more hydrophilic biopolymers.

The astringent that can be used in the context of the present invention is generally chosen from the group consisting of iron or aluminum chlorides and sulfates, potassium aluminum sulfate, and mixtures thereof.

In the currently preferred embodiment of the invention, the astringent is aluminum chloride and can be used in an amount advantageously between 7 and 10% by weight, relative to the total weight of the insertion material.

The amount of water contained in the insertion material in accordance with the invention can vary, in particular according to the nature of the texturizing agent and to whether or not it is combined with a humectant.

Water, preferably purified water, is used in an amount sufficient to obtain a cohesive paste having the physicochemical characteristics which are subsequently detailed.

Generally, the water is present in the insertion material in an amount of between 30 and 60% by weight, preferably between 30 and 55% by weight, relative to the total weight of the material.

The humectant that can be used in the context of the present invention is generally chosen from the group consisting of glycerol, polyethylene glycol and sorbitol, and mixtures thereof. It will preferably be glycerol (or glycine).

The humectant does not constitute an essential component of the insertion material according to the invention. It is advantageously used to improve the stability of the insertion material, in particular to prevent this material from drying out during storage thereof.

When it is used, the humectant is present in the material in an amount of generally between 5 and 18% by weight, preferably between 8 and 16% by weight, relative to the total weight of the material.

The insertion material in accordance with the invention is free of kaolin, at the very least in any significant proportion, for example greater than 10% by weight relative to the total weight of the material.

The insertion material in accordance with the present invention can also comprise up to 1% by weight, and preferably from 0.01 to 0.5% by weight of at least one additive chosen from dyes and flavorings, preferably of food grade.

Any type of dye can be used in the context of the present invention.

As regards dental applications, a dye that has a color which stands out clearly against the color of the tooth and of the gum, for instance blue, yellow or green, will preferably be used.

The dye can be used in an amount of generally between 0.005% and 0.05%, preferably of approximately 0.01% by weight, relative to the total weight of the material.

There is also no limitation as to the nature of the flavoring that can be used in the context of the present invention. It may be an almond, mint or lemon flavoring, for example.

The amount of flavoring that can be used is generally between 0.1 and 1%, and preferably approximately 0.5% by weight, relative to the total weight of the material.

The insertion material in accordance with the invention may also comprise up to 10% by weight, and preferably from 2 to 10% by weight, of at least one active substance chosen from local anesthetics.

Among the local anesthetics that can be used in the context of the invention, mention may be made of lidocaine, prilocaine, bupivacaine, benzoin, tetracaine, mepivacaine and ropivacaine.

Advantageously, the local anesthetic is lidocaine and can be used in an amount of approximately 2 to 7% by weight, relative to the total weight of the material.

The insertion material in accordance with the present invention has original physicochemical properties which allow it to meet the requirements of its use in the dental field, in particular for widening the gingival crevice.

Thus, this material has, first of all, and this constitutes an original technical feature of the present invention, a specific dissolution profile in an aqueous medium that can be measured by the specific release of the astringent.

More specifically, the amount of astringents released, measured according to the dissolution method described in the European Pharmacopoeia, 6th edition (Ph. Eur. 2.9.3 (01/2008)) at 150 rpm in 700 ml of purified water at 37° C., is:
  less than 20% after 5 min;
  less than 40%, and preferably less than 30% after 10 min;
  less than 50%, and preferably less than 40% after 15 min;
  less than 60%, and preferably less than 55% after 30 min;
  less than 80%, and preferably less than 70% after 60 min.

The amount of astringent released can be determined by assaying methods well known to those skilled in the art.

In the case of aluminum chloride, which constitutes the astringent currently preferred, this assay can be carried out by complexometric titration, for example according to the method described in the European Pharmacopoeia, 6th edition (01/2008) in chapter 2.5.11.

It has been shown that the insertion material in accordance with the present invention releases the astringent much more slowly than the Expasyl® product, and therefore allows prolonged use in the mouth.

By way of example, the amount of astringent released after 10 min with the Expasyl® product is approximately 55%, whereas this same amount is less than 40%, or even less than 30% with a material according to the invention.

Moreover, the insertion material in accordance with the present invention exhibits excellent cohesion over time. Thus, this material shows no visible disintegration after 5 h according to the method for disintegration of tablets and capsules described in the European Pharmacopoeia, 6th edition (01/2008) in chapter 2.9.1, for a sample having a diameter of 10 mm and a thickness of 4 mm and a disintegration medium consisting of purified water at 37° C.

In the same test, it was noted that the Expasyl® material disintegrates completely after 15 min.

Finally, extrusion, compression and shear tests have shown that the insertion material according to the invention has at least one of the following mechanical properties:
  an essentially plastic rheological behavior;
  a sliding tribological behavior with a threshold friction, preferably between 10 and 60 kPa;
  an initial shear threshold of between 30 and 350 kPa;
  a Young's modulus of between 65 and 200 kPa.

The insertion material in accordance with the present invention can be readily produced by simple mixing of its constituents.

Generally, an insertion material according to the invention can be obtained by mixing:
  firstly, a mixture containing purified water and the astringent and, optionally, a humectant such as glycerol and a dye such as patent blue; and
  secondly, a mixture containing a texturizing agent such as a polysaccharide, preferably of iota-carrageenan type, optionally combined with a plant fiber and/or with polyvinyl alcohol.

The invention will be understood more clearly on reading the following nonlimiting examples.

EXAMPLE 1

Step 1: In a 40 l beaker made of low-density polyethylene, 16.758 liters of water purified according to the European Pharmacopoeia 6.3 standard (01/2009:0008) and 9.027 kg of aluminum chloride hexahydrate (Panreac) were mixed and stirred for 10 minutes using a retractable-blade pneumatic stirrer. Owing to the exothermicity of the reaction between the water and the aluminum chloride, all necessary precautions known to those skilled in the art must be used.

15 g of patent blue (Spectracol) were then gradually added with stirring into the vortex of the abovementioned mixture, and the resulting mixture was stirred for 10 minutes using the pneumatic stirrer until the solution was homogeneous.

Still with stirring, 8.4 kg of glycerol (La Cooper) were then added into the vortex of the mixture, and the stirring was maintained for a further 10 minutes using the pneumatic stirrer.

Step 2: All of the mixture prepared in step 1, 14.4 kg of oat fibers and 11.4 kg of carrageenans of Viscarin° PC 389 type were introduced into the tank of a Z-arm blender equipped with a cooling system (circulation of cold water in the double jacket), and then pre-mixed at a speed of 19 rpm for 20 minutes.

The blender can be optionally stopped so as to detach the paste from the walls of the blender.

The resulting mixture is then stirred for a further period of 40 minutes at a speed of 19 rpm, thus producing an insertion material according to the invention.

EXAMPLES 2 to 5

Various materials according to the invention were prepared by following a process analogous to that described in example 1. The composition of each of the materials prepared is given as percentage by weight relative to the total weight of the material in the following table I.

TABLE I

|  | Example 2 | Example 3 | Example 4 | Example 5 |
|---|---|---|---|---|
| Water | 46.56 | 37 | 36.35 | 41 |
| Polyvinyl alcohol | 2 |  |  | 1 |
| AlCl$_3$ | 9.44 | 9 | 9.06 | 9 |
| Glycerol | 10 | 10 | 15.71 | 15 |
| Carrageenan [1] |  | 44 | 17.27 | 8 |
| Oat fiber |  |  | 21.58 | 11 |
| Pea fiber | 32 |  |  | 15 |
| Dye |  |  | 0.03 |  |
| Total | 100 | 100 | 100 | 100 |

[1] Viscarin ® PC 389 sold by the company FMC Biopolymere.

EXAMPLE 6

Demonstration of the Physicochemical Properties of the Material According to the Invention Dissolution Tests
Protocol Used:
  Protocol followed: European Pharmacopoeia 2.9.3 "Dissolution test for solid dosage forms"
  Type of device used: Sotax paddle apparatus
  Paddle rotational speed: 150 rpm
  Thermostated bath temperature: 37° C.
  Tank volume=700 ml Dissolution medium sampling mode:
time: t=5 min, 10 min, 15 min, 30 min,
method: samples taken using a graduated glass pipette of class A+ precision
sample volume=50 ml
Method of analysis: Complexometric titration (according to European Pharmacopoeia 2.5.11)

Results Obtained:

The dissolution results obtained with the material of example 1 were compared with those obtained with the Expasyl® product. These results, which have been reported in table II and in FIG. 1, show very clearly that the materials according to the invention have a dissolution rate characterized by a significantly slower release of the astringent than in the case of Expasyl®.

TABLE II

| Time (min) | 5 | 10 | 15 | 30 | 60 |
|---|---|---|---|---|---|
| Expasyl | 22.72 | 55.18 | 74.65 | 84.27 | 95.50 |
| Example 1 | 15.80 | 23.13 | 31.60 | 47.11 | 58.40 |

Disintegration Test tests carried out according to the European Pharmacopoeia 2.9.1 (disintegration of tablets and capsules); test A—tablets and capsules of normal sizes with use of cylindrical disks
immersion temperature: 37° C.
immersion medium: water purified according to the European Pharmacopoeia 6.3 standard (01/2009:0008)
sample diameter: 10 mm
sample thickness: 4 mm
disintegration resistance: 5 hours Extrusion and Shear Tests The extrusion tests were carried out using a cylindrically shaped cartridge, 30 mm long and 4.5 mm in diameter, and having a conical convergent shape at the end of the die exhibiting a reduction ratio close to 0.5 and an angle of 45°. The extrusion tests were carried out by means of a texture analyzer, for two applied piston speeds, respectively 1 and 3 mm/s.

The values of friction stress and shear threshold (kPa) and also the internal friction coefficients (kPa/mm) were determined for a sample of formulations according to the invention and are reported in the following table III:

TABLE III

|  | Example 2 | Example 3 | Example 4 |
|---|---|---|---|
| Friction stress at 1 mm/s | 15.6 | 16.7 | 12.0 |
| Friction stress at 3 mm/s | 18.3 | 25.9 | 10.9 |
| Shear threshold at 1 mm/s | 97.6 | 78.3 | 63.2 |
| Shear threshold at 3 mm/s | 118.5 | 99.5 | 80.2 |
| Internal friction coefficient | 10.4 | 10.6 | 10.6 |

The direct-shear tests were carried out by means of a Brookfield Soft Solid Tester rheometer equipped with a four-bladed vane geometry with a diameter of 5 mm and a height of 10 mm. Thus, the influence of the rotational speed of the apparatus on the static threshold (or flow point) and the dynamic threshold were studied.

These tests made it possible to emphasize:
firstly, that the materials of the invention have an even friction over approximately 90% of the length of the cartridge tube; and
secondly, that these materials exhibit an essentially plastic rheological behavior and a sliding tribological behavior with a threshold friction. The plasticity and friction thresholds appear to be influenced by the speed, without it being possible for the effect to be assimilated to a viscosity.

The invention claimed is:

1. An insertion material for widening a gingival crevice, wherein the insertion material consists of a hydrophilic paste comprising, expressed as percentage by weight relative to the total weight of the material:
   between 5 and 15% of an astringent;
   between 25 and 50% of a texturizing agent chosen from:
      a hydrophilic biopolymer;
      a hydrophilic biopolymer combined with a plant fiber;
      a hydrophilic biopolymer combined with a plant fiber and polyvinyl alcohol; and
      a plant fiber combined with polyvinyl alcohol;
   between 30 and 60% of water; and
   between 0 and 20% of a humectant;
   the total amount of water and the humectant being between 35 and 65% by weight relative to the total weight of the material; and
   said insertion material having the following release profile for the astringent, measured according to the dissolution method described in the European Pharmacopoeia, 6th edition (Ph. Eur. 2.9.3 (01/2008)) at 150 rpm in 700 ml of purified water at 37° C.:
   less than 20% of the astringent released after 5 min;
   less than 40% of the astringent released after 10 min;
   less than 50% of the astringent released after 15 min;
   less than 60% of the astringent released after 30 min; and
   less than 80% of the astringent released after 60 min.

2. The insertion material as claimed in claim 1, wherein the hydrophilic paste comprises, expressed as percentage by weight relative to the total weight of the material:
   between 6 and 12% of the astringent;
   between 30 and 45% of the texturizing agent;
   between 30 and 55% of water; and
   between 5 and 18% of the humectant;
   the total amount of water and the humectant being between 40 and 60% by weight relative to the total weight of the material.

3. The insertion material as claimed in claim 1, wherein the insertion material has the following release profile for the astringent:
   less than 20% of the astringent released after 5 min;
   less than 30% of the astringent released after 10 min;
   less than 40% of the astringent released after 15 min;
   less than 55% of the astringent released after 30 min; and
   less than 70% of the astringent released after 60 min.

4. The insertion material as claimed in claim 1, wherein the hydrophilic biopolymer is a polysaccharide of natural origin having a gelling or a thickening capability.

5. The insertion material as claimed in claim 1, wherein the plant fiber is chosen from a pea fiber and an oat fiber.

6. The insertion material as claimed in claim 1, wherein the astringent is at least one selected from the group consisting of iron chloride, iron sulfate, aluminum chloride and aluminum sulfate.

7. The insertion material as claimed in claim 6, wherein the astringent is at least one selected from the group consisting of aluminum chloride and iron chloride.

8. The insertion material as claimed in claim 1, wherein the humectant is at least one selected from the group consisting of glycerol, polyethylene glycol and polyethylene sorbitol.

9. The insertion material as claimed in claim 7, wherein the humectant is glycerol.

10. The insertion material as claimed in claim 1, wherein the hydrophilic paste further comprises up to 1% by weight of at least one additive chosen from dyes and flavorings.

11. The insertion material as claimed in claim 1, wherein the hydrophilic paste further comprises up to 10% by weight a local anesthetic.

12. The insertion material as claimed in claim 1, wherein the insertion material has at least one of the following characteristics:
    a plastic rheological behavior;
    a sliding tribological behavior with a threshold friction;
    an initial shear threshold of between 30 and 350 kPa; and
    a Young's modulus of between 65 and 200 kPa.

13. The insertion material as claimed in claim 1, wherein the astringent is aluminum chloride.

14. The insertion material as claimed in claim 4, wherein the polysaccharide is of food grade.

15. The insertion material as claimed in claim 2, wherein the polysaccharide is at least one selected from the group consisting of pectins, galactomannans of guar, locust bean, tara seeds, scleroglucan, xanthan and carrageenans.

16. The insertion material as claimed in claim 15, wherein the carrageenans are of an iota type.

17. The insertion material as claimed in claim 6, wherein the aluminum sulfate is potassium aluminum sulfate.

18. The insertion material as claimed in claim 10, wherein the dyes and flavorings are of food grade.

19. The insertion material as claimed in claim 10, wherein the at least one additive is included in an amount from 0.01 to 0.5% by weight.

20. The insertion material as claimed in claim 11, wherein the local anesthetic is lidocaine.

21. The insertion material as claimed in claim 11, wherein the local anesthetic is included in an amount from 2 to 10% by weight.

22. The insertion material as claimed in claim 12, wherein the threshold friction is between 10 and 60 kPa.

23. The insertion material as claimed in claim 1, wherein the insertion material is free of kaolin.

24. An insertion material for widening a gingival crevice, wherein the insertion material consists of a hydrophilic paste comprising, expressed as percentage by weight relative to the total weight of the material:
    between 5 and 15% of an astringent;
    between 25 and 50% of a texturizing agent chosen from:
        a hydrophilic biopolymer;
        a hydrophilic biopolymer combined with a plant fiber;
        a hydrophilic biopolymer combined with a plant fiber and polyvinyl alcohol; and
        a plant fiber combined with polyvinyl alcohol;
    between 30 and 60% of water; and
    between 0 and 20% of a humectant;
    the total amount of water and the humectant being between 35 and 65% by weight relative to the total weight of the material; and
    said insertion material having the following release profile for the astringent, measured according to the dissolution method described in the European Pharmacopoeia, 6th edition (Ph. Eur. 2.9.3 (01/2008)) at 150 rpm in 700 ml of purified water at 37° C.:
    less than 20% of the astringent released after 5 min;
    less than 40% of the astringent released after 10 min;
    less than 50% of the astringent released after 15 min;
    less than 60% of the astringent released after 30 min; and
    less than 80% of the astringent released after 60 min
    wherein the hydrophilic biopolymer is a polysaccharide that is at least one selected from the group consisting of pectins, galactomannans of guar, locust bean, tara seeds, scleroglucan, and carrageenans.

25. The insertion material as claimed in claim 24, wherein the polysaccharide is selected from carrageenans.

* * * * *